(12) United States Patent
Padrela et al.

(10) Patent No.: US 12,357,956 B2
(45) Date of Patent: Jul. 15, 2025

(54) PARTICLE COATING METHOD

(71) Applicant: University of Limerick, Limerick (IE)

(72) Inventors: Luis Padrela, Limerick (IE); Kevin Ryan, Limerick (IE)

(73) Assignee: University of Limerick, Limerick (IE)

( * ) Notice: Subject to any disclaimer, the term of this patent is extended or adjusted under 35 U.S.C. 154(b) by 3 days.

(21) Appl. No.: 17/904,525

(22) PCT Filed: Feb. 19, 2021

(86) PCT No.: PCT/EP2021/054234
§ 371 (c)(1),
(2) Date: Aug. 18, 2022

(87) PCT Pub. No.: WO2021/165513
PCT Pub. Date: Aug. 26, 2021

(65) Prior Publication Data
US 2023/0090969 A1 Mar. 23, 2023

(30) Foreign Application Priority Data
Feb. 19, 2020 (GB) ..................... 2002325

(51) Int. Cl.
*B01J 2/00* (2006.01)
*A61K 31/192* (2006.01)
(Continued)

(52) U.S. Cl.
CPC ............. *B01J 2/006* (2013.01); *A61K 31/192* (2013.01); *A61K 31/519* (2013.01);
(Continued)

(58) Field of Classification Search
None
See application file for complete search history.

(56) References Cited

U.S. PATENT DOCUMENTS

2006/0039983 A1\* 2/2006 Shekunov ............ A61K 9/1694
424/489
2006/0210640 A1 9/2006 Kerkhof
(Continued)

FOREIGN PATENT DOCUMENTS

JP 2004298721 A 10/2004
WO 9931019 A1 6/1999
(Continued)

OTHER PUBLICATIONS

Q. Li et al., Chemical Engineering Journal, 2017, 313, 317-327.
(Continued)

*Primary Examiner* — Shamim Ahmed
*Assistant Examiner* — Bradford M Gates
(74) *Attorney, Agent, or Firm* — Husch Blackwell LLP (57) ABSTRACT

A method of producing a particle coating on one or more items is provided. The method comprises mixing a supercritical fluid with a solution comprising dissolved material for forming particles. The method further comprises spraying the mixture into a precipitation chamber (316) to precipitate particles, wherein the chamber is at a pressure below a supercritical pressure of the supercritical fluid. The method comprises conveying items to be coated from an inlet of the chamber to an outlet of the chamber. The method also comprises capturing the precipitated particles on items within the chamber.

19 Claims, 5 Drawing Sheets

(51) Int. Cl.
*A61K 31/519* (2006.01)
*A61K 31/549* (2006.01)
*A61K 31/55* (2006.01)
*A61K 47/10* (2017.01)

(52) U.S. Cl.
CPC ............ *A61K 31/549* (2013.01); *A61K 31/55* (2013.01); *A61K 47/10* (2013.01); *B01J 2/003* (2013.01)

(56) References Cited

U.S. PATENT DOCUMENTS

| | | | |
|---|---|---|---|
| 2013/0071665 A1* | 3/2013 | Harada | ................... C08L 83/06 428/407 |
| 2015/0000846 A1 | 1/2015 | Risse et al. | |
| 2016/0346206 A1 | 12/2016 | Costa et al. | |
| 2018/0221849 A1 | 8/2018 | Johnson et al. | |
| 2019/0016962 A1* | 1/2019 | Gupta | ................... B01F 33/404 |

FOREIGN PATENT DOCUMENTS

| | | |
|---|---|---|
| WO | 2015053857 | 4/2015 |
| WO | 2016156841 | 10/2016 |

OTHER PUBLICATIONS

Matos et al., Journal of Supercritical Fluids, 2018, 141, 143-156.
Leeke et al., Journal of Supercritical Fluids, 2014, 91, 7-14.
International Search Report and Written Opinion for International Application No. PCT/EP2021/054234 issued on May 7, 2021, 11 pages.

* cited by examiner

FIGURE 1

```
┌─────────────────────────────┐
│ Compress carbon dioxide gas │
│ to a liquid state           │
└─────────────────────────────┘
 202  │
      ▼
┌─────────────────────────────┐
│ Temporarily store compressed│
│ carbon dioxide in a vessel  │
└─────────────────────────────┘
 204  │
      ▼
┌─────────────────────────────┐
│ Deliver compressed carbon   │
│ dioxide to at least one     │
│ nozzle                      │
└─────────────────────────────┘
 206  │
      ▼
┌─────────────────────────────┐
│ Deliver solution comprising │
│ dissolved material for      │
│ forming nanoparticles to    │
│ the at least one nozzle     │
└─────────────────────────────┘
 208  │
      ▼
┌─────────────────────────────┐
│ Mix supercritical carbon    │
│ dioxide with solution in    │
│ the nozzle                  │
└─────────────────────────────┘
 210  │
      ▼
┌─────────────────────────────┐
│ Spray mixture through the   │
│ nozzle into a precipitation │
│ chamber held at atmospheric │
│ pressure                    │
└─────────────────────────────┘
 212  │
      ▼
┌─────────────────────────────┐
│ Introduce a flow of drying  │
│ gas to the chamber          │
└─────────────────────────────┘
 214  │
      ▼
┌─────────────────────────────┐        ┌──────────────────────────┐
│ Continuously introduce      │        │ Collect coated carrier   │
│ carrier particles to be     │        │ particles                │
│ coated into the chamber     │        └──────────────────────────┘
└─────────────────────────────┘         220       ▲
 216  │                                           │
      │                                  ┌──────────────────────────┐
      └─────────────────────────────────▶│ Capture precipitated     │
                                         │ nanoparticles on the     │
                                         │ carrier particles        │
                                         └──────────────────────────┘
                                          218
```

PARTICLE COATING METHOD

FIELD OF THE INVENTION

The present invention relates to a method for producing a particle coating on one or more items, and in particular but not exclusively for producing a nanoparticle coating on carrier particles.

BACKGROUND

Particles such as nanoparticles of active pharmaceutical ingredients (API) provide advantageous properties such as improved solubility, dissolution rate and bioavailability when compared to conventional larger API particles. However, particles such as nanoparticles are not readily produced, stabilized and isolated using conventional techniques. Where further reduction of API nanoparticle size below 500 nm is required, that typically compromises the physiochemical properties of the API nanoparticles (including rheological properties such as flowability and compressibility).

Top down techniques for generating nanoparticles include milling and high-pressure homogenisation, while bottom-up techniques include liquid and supercritical anti-solvent precipitation, and conventional nano-spray drying (for example using nitrogen). However, existing techniques for isolating API nanoparticles by coating onto carrier particles are limited in terms of controlling characteristics such as API particle size precipitated onto the carrier particles, agglomeration of API particles coated onto the carrier particles, API particle solid-state (amorphous or crystalline), API particle loading into or onto carrier particles, and low product yield due to inefficient collection of the API particles.

In particular, the supercritical anti-solvent (SAS) technique has emerged as a potential technique to produce API nanoparticles with controlled particle shape and particle size distribution. The API nanoparticles may be coated onto carrier particles located inside a pressurized drying chamber. However, this process requires high pressure inside the drying chamber which limits its scalability and jeopardizes safety of the process.

The present invention has been devised with the foregoing in mind.

SUMMARY

According to a first aspect, there is provided a method of producing a particle coating on one or more items. The method may comprise mixing a supercritical fluid such as supercritical carbon dioxide with a solution comprising material such as dissolved material for forming particles. The method may also comprise spraying the formed mixture into a precipitation chamber to precipitate particles. The chamber may be at a pressure below a supercritical pressure of the supercritical fluid (below a threshold pressure required to maintain the supercritical fluid in a supercritical state). The chamber may be at substantially atmospheric pressure. The method may comprise conveying items to be coated from an inlet of the chamber to an outlet of the chamber. The method may comprise capturing the precipitated particles on items within (for example in or travelling through) the chamber.

Mixing a supercritical fluid such as supercritical carbon dioxide with a solution comprising dissolved material for producing particles prior to introducing the formed mixture to a precipitation chamber may allow the chamber to be held at a pressure below a threshold pressure required to maintain the supercritical fluid in a supercritical state (for example, at atmospheric pressure). The supercritical fluid in the mixture may act as either or both of a supercritical anti-solvent and an atomization enhancer. A rapid pressure drop as the mixture is sprayed into the chamber may cause droplets of the solution to be formed as the supercritical fluid depressurizes. Due to the below supercritical pressure (for example, atmospheric pressure) in the chamber, the droplets may then rapidly dry (for example, prior to contacting the one or more items within the chamber) to form particles. Momentum of the depressurized carbon dioxide may also provide a drying effect for the droplets. The pressure (for example atmospheric pressure) of the chamber may therefore provide a dual effect in aiding the precipitation of particles.

Previous approaches employing a supercritical anti-solvent process often require a high pressure environment to produce particles. Typically, a solution comprising dissolved material for forming particles is introduced to a chamber that already contains supercritical fluid. That requires the chamber to be sufficiently pressurized to maintain the supercritical fluid in a supercritical state. Maintaining a high pressure environment requires specialized high pressure equipment, which increases equipment costs and jeopardizes scalability and process safety. It also typically limits such approaches to batch production. Alternative previous approaches include dissolving the material for producing particles directly into supercritical carbon dioxide and using a low pressure chamber to precipitate particles (known as rapid expansion of supercritical solution, or RESS). However, solubility in supercritical fluid such as supercritical carbon dioxide is very low for some materials. That limits the applicability of RESS processes, as the throughput is low and the process must be carried out for a longer time.

By mixing a supercritical fluid such as supercritical carbon dioxide with a solution comprising dissolved material for forming nanoparticles prior to introducing the formed mixture to a precipitation chamber, precipitation of particles may be carried out below supercritical pressure of the supercritical fluid (for example at atmospheric pressure), and cost and complexity of the process and equipment may be reduced. An advantage of atmospheric pressure may be that no specialist equipment (for example pumps) for pressurizing or providing a vacuum within the chamber is required. The chamber may also not be required to support a substantial pressure differential between an internal volume of the chamber and an external environment. In addition, the method may avoid dissolving the material for forming particles directly in supercritical fluid such as supercritical carbon dioxide, which may increase throughput and/or process efficiency.

Capturing the precipitated particles on one or more items located within the chamber soon after precipitation may reduce opportunity for the particles to agglomerate or coalesce. The particles may therefore be coated onto the one or more items substantially individually, resulting in a homogeneous particle coating. That may be particularly beneficial for nanoparticle coatings. Nanoparticles have a tendency to agglomerate which can have a deleterious effect on rheological properties of the nanoparticles such as compressibility and flowability. Integrating particle production and particle coating into a single process may avoid the need for intermediate steps to isolate the particles prior to coating (such as the use of filters or electrostatic chambers). Capturing the precipitated particles soon after precipitation may also improve the process yield (particularly in respect of nanoparticles).

Conveying items to be coated from an inlet of the chamber to an outlet of the chamber may enable the method to be operated continuously. A continuous process for producing a particle coating on one or more items may improve process efficiency. A continuous process may result in less downtime, improving cost and time efficiency of the process. In addition, a continuous process may result in less variation in operating conditions. Consistency of process operating conditions or parameters may lead to better, more consistent properties and behaviour of the coated items. A continuous process may be enabled by the chamber being held at atmospheric pressure. That may avoid the need to depressurize the chamber in order to remove coated items located within the chamber.

The method may comprise introducing the items substantially from a top portion of the chamber. The method may comprise capturing precipitated particles on the one or more items as the items travel through the chamber by falling under gravity. The method may comprise collecting items coated with precipitated particles and removing them from the chamber. The items coated with precipitated particles may be removed from the chamber continuously or intermittently. Removal of the items coated with precipitated particles may prevent build-up of coated items in the chamber.

The method may comprise gravity feeding items to be coated into the chamber. The method may comprise introducing the items from a top portion of the chamber.

Gravity feeding the one or more items to be coated into the chamber may be a simple, low cost way of implementing feeding of items into the chamber. Gravity feeding may also enable simple, continuous introduction of items to be coated into the chamber. The one or more items may be coated with particles as the items travel through the chamber from substantially a top portion of the chamber by falling under gravity.

The method may comprise selecting or controlling a feed rate of items introduced to the chamber. The method may comprise selecting or controlling a removal rate of items coated with precipitated particles from the chamber. The feed rate and the removal rate may be substantially identical on average (for example, to account for intermittent removal of coated items). Alternatively, the removal rate may be fixed. The feed rate may have a threshold feed rate above which the feed rate may not be increased. The threshold feed rate may be substantially identical to the fixed removal rate.

Controlling a feed rate of items introduced into the chamber may enable particle loading onto items to be controlled. A higher feed rate may result in a lower particle loading onto the one or more items. Conversely, a lower feed rate may result in a higher particle loading onto the one or more items. Feed rate may be controlled independently of other operational parameters. Alternatively, feed rate may be controlled in conjunction with one or more other parameters such as solution concentration and flow rate of solution. A higher solution concentration may result in a higher particle loading onto the one or more items, and vice versa. Similarly, a higher flow rate of solution may result in a higher particle loading onto the one or more items, and vice versa. A higher solution concentration and a higher flow rate of solution may both result in a greater mass of material for forming particles being introduced to the chamber. Introducing a greater mass of material for forming particles into the chamber may increase the possible amount of particle material that may be captured by the one or more items.

The method may comprise spraying the mixture through at least one nozzle into the chamber to precipitate particles. A particle size produced by the method may be determined or controlled by a nozzle orifice size of the at least one nozzle (a size of one or more openings in the at least one nozzle) through which the mixture is sprayed. Larger nozzle orifices may produce larger droplets of solution as the mixture enters the precipitation chamber, whereas smaller nozzle orifices may produce smaller droplets of solution as the mixture enters the precipitation chamber. A nozzle orifice size may be selected so as to produce nanodroplets (nanosized droplets) when spraying the mixture into the precipitation chamber, resulting in the precipitation of nanoparticles. For example, the nozzle orifice size may be substantially 150 μm or smaller to precipitate nanoparticles, and optionally may be substantially 50 μm, and further optionally may be substantially 40 μm. The nanoparticles may be sized between substantially 10 nm and substantially 500 nm, and may be sized between substantially 90 nm and substantially 500 nm. Any suitable nozzle orifice size may be used to produce particles of a desired size.

The method may comprise capturing the precipitated particles on one or more items such as carrier particles. The carrier particles may be or comprise one or more excipients. The one or more excipients may be or comprise microcrystalline cellulose. The solution may be or comprise an active pharmaceutical ingredient (API) or an anti-bacterial drug. The API or anti-bacterial drug may be dissolved in an organic solvent. The API may be or comprise an ingredient or drug from any class (class I, class II, class III or class IV) according to the biopharmaceutical classification system (BCS). The API may be or comprise one or more of carbamazepine, risperidone, ketoprofen and hydrochlorothiazide. The organic solvent may be or comprise an alcohol, for example methanol.

By selecting an appropriate nozzle orifice size, a homogeneous coating of API nanoparticles may be provided on excipient carrier particles. Providing excipient carrier particles with a homogeneous coating of individual API nanoparticles using the above method may result in coated carrier particles without requiring any additional processing steps. The coated carrier particles may have optimal rheological properties (for example, flowability or compressibility) typical of larger micron sized particles, whilst maintaining high solubility and dissolution rate profiles typical of nanosized API particles. The coated carrier particles may undergo direct compression into final oral dosage form (for example, tablet form). The method may therefore enhance the effectiveness and processability of APIs.

The method may comprise mixing supercritical fluid such as supercritical carbon dioxide with a first solution comprising a first dissolved material for forming particles to form a first mixture. The method may comprise spraying the first mixture into the chamber to precipitate particles of a first material. The method may also comprise mixing supercritical fluid such as supercritical carbon dioxide with a second solution comprising a second dissolved material for forming particles to form a second mixture. The method may comprise spraying the second mixture into the chamber to precipitate particles of a second material.

Coating items with multiple different particle types may enable combinations or tailoring of properties. For example, if the particles are or comprise multiple different API nanoparticles, multiple APIs may be coated onto excipient carrier particles. That may enable personalised drug combinations which may reduce the number of tablets an individual is required to take.

Alternatively, for non-medical or non-medicinal applications, multiple different particle types may enable, for example, one or more of mechanical properties, chemical properties, electrical properties, thermal properties and optical properties of a coating to be tailored. In particular, controlling concentration of different solutions or flow rates of different solutions may enable the proportions of each particle type to be varied in order to tailor the coating properties.

The method may comprise introducing a flow of drying gas into the chamber. The supercritical anti-solvent and/or atomisation enhancement properties of supercritical fluid such as supercritical carbon dioxide may assist or enhance a spray-drying process.

The formation of droplets due to the rapid pressure drop experienced by the mixture as it passes through the nozzle means that solvent evaporation may be rapid, resulting in rapid precipitation of particles. Integrating supercritical anti-solvent behaviour with a spray-drying process may further increase a rate of solvent evaporation. That may further enable particles to be rapidly produced.

Typically, spray-drying can be used to form micron sized particles (conventional spray-drying) or nanosized particles (nano spray-drying). As discussed above, nanoparticles often agglomerate if not isolated or captured on an item to be coated soon after being produced. That can result in a low processing yield for nano spray-drying, and subsequently a non-homogeneous coating on one or more coated items due to agglomerated nanoparticles. Integrating spray-drying and particle coating into a single process may improve process yield and provide a substantially homogeneous particle coating.

The drying gas may be or comprise one or more of carbon dioxide and nitrogen.

The method may comprise introducing a flow of drying gas substantially from a top portion of the chamber. The flow of drying gas may therefore be oriented to avoid the flow of drying gas opposing or even reversing a direction of travel of items within the chamber (which may disrupt a continuous coating process).

The method may comprise introducing a flow of drying gas substantially from a side portion of the chamber. Introducing the flow of drying gas from a side portion of the chamber may prevent interference with feeding items from a top portion of the chamber. The flow of drying gas may be oriented to promote a helical travel path of items and precipitated particles through the chamber. That may increase a circulation time of either of both of the one or more items and the precipitated particles within the chamber compared to a direct linear travel path through the chamber. Increasing a circulation time may improve one or more of drying of the items, drying of the particles and particle loading onto the items during a continuous coating process.

The method may comprise introducing a flow of drying gas from a plurality of locations on substantially a side portion of the chamber (for example, from a plurality of inlets in substantially a side portion of the chamber). The plurality of locations may be distributed over a circumference or perimeter of the chamber. Additionally or alternatively, the plurality of locations may be distributed over a length or height of the chamber. The plurality of locations may be arranged to orient the flows of drying gas to cooperate with one another to promote a helical travel path of items and precipitated particles through the chamber. The plurality of locations may be distributed uniformly or non-uniformly across a side portion of the chamber. The plurality of locations may be arranged in a substantially helical pattern across a side portion of the chamber. In addition or alternatively to increasing a circulation time within the chamber (for example, by promoting a helical travel path of items and precipitated particles through the chamber), a plurality of flows of drying gas oriented in a number of different directions may prevent or inhibit precipitated particles from being captured on internal walls of the chamber. The precipitated particles and items may be substantially confined to a region of the chamber away from the walls by differently oriented flows of drying gas. That may increase a likelihood of the precipitated particles being captured on one or more items within the chamber, increasing process yield and efficiency.

The method may comprise collecting items coated with precipitated particles using a cyclone separator. The cyclone separator may be disposed within the chamber, or may be located externally of the chamber. The cyclone separator may be in fluid communication with the chamber. Using a cyclone separator may enable efficient separation and collection of items coated with precipitated particles, particularly in a continuous coating process.

The method may comprise spraying the mixture substantially from a side portion of the chamber. Spraying the mixture from a side portion of the chamber may prevent interference with feeding the items from a top portion of the chamber, which may occur if spraying the mixture from a top portion of the chamber. That may enhance simplicity of the process. The spray of the mixture may be oriented to promote a helical travel path of items and precipitated particles through the chamber. That may increase a circulation time of the items and precipitated particles within the chamber compared to a direct linear travel path through the chamber (for example, an item falling under gravity without other forces being applied would follow a substantially linear path through the chamber). Increasing a circulation time may improve one or more of drying of the items, drying of the precipitated particles and particle loading onto the items.

The method may comprise spraying the mixture from a plurality of locations substantially on a side portion of the chamber (for example, using a plurality of nozzles). The plurality of locations may be distributed over a length or height of the chamber. As the items travel through the chamber (for example, falling under gravity from a top portion of the chamber), the items may be coated with progressively more and more particles from successive sprays as the items approach a bottom of the chamber. Spraying the mixture only from a top portion of the chamber would result in items fed into the chamber falling increasingly further away from precipitated nanoparticles, providing only a small spatial area within the chamber for items to be efficiently coated. Spraying the mixture from a plurality of locations distributed over a length or height of the chamber may overcome that issue, as particles are precipitated at multiple locations along the items' travel path through the chamber.

Additionally or alternatively, the plurality of locations may be distributed over a circumference or perimeter of the chamber. The plurality of locations may be arranged to orient the mixture sprays to cooperate with one another to promote a helical travel path of items and precipitated particles through the chamber. The plurality of locations may be uniformly or non-uniformly distributed across a side portion of the chamber. The plurality of locations may be arranged in a substantially helical pattern across a side portion of the chamber.

A plurality of mixture sprays oriented in a number of different directions may improve homogeneity of the particle coating. That may also prevent or inhibit precipitated particles from being captured on internal walls of the chamber. The precipitated particles and items may be substantially confined to a region of the chamber away from the walls by differently oriented sprays of mixture from the plurality of locations. That may increase a likelihood of the precipitated particles being captured on one or more items within the chamber, increasing process yield and efficiency.

The method may comprise promoting a helical travel path of items and precipitated particles through the chamber by one or more sprays of mixture from one or more nozzles cooperating with one or more flows of drying gas.

The solution may be or comprise a saturated solution. In this specification, the term 'saturated' means that a concentration of the solution is near to but not above its saturation limit. A saturated solution may enable the formation of crystalline particles. Conversely, an undersaturated solution may result in the formation of amorphous particles, whilst a supersaturated solution may result in the formation of crystalline particles but may cause blockage of a nozzle through which the mixture may be sprayed.

The method may comprise controlling a concentration of the solution comprising dissolved material for forming particles. Controlling the concentration of the solution may enable particle loading (e.g., a mass of particle coating relative to a mass of the one or more items) on the one or more items to be altered. An increased concentration of the solution may enable increased particle loading on the one or more items. Additionally or alternatively, the method may comprise controlling a flow rate of the solution comprising dissolved material for forming particles to adjust particle loading on the one or more items. Similarly, a feed rate of the one or more items may be selected or controlled to adjust particle loading on the one or more items.

The method may comprise mixing the supercritical fluid such as supercritical carbon dioxide with the solution in a nozzle. The nozzle may be or comprise a high pressure nozzle. Alternatively or additionally, the nozzle may be or comprise a coaxial nozzle.

The method may alternatively comprise coating one or more items such as medical implants, for example joint replacement implants or stents.

According to a second aspect, there is provided an apparatus for producing a particle coating on one or more items. The apparatus may comprise a chamber. The apparatus may comprise at least one nozzle to spray a mixture of supercritical fluid such as supercritical carbon dioxide and a solution comprising dissolved material for forming particles into the chamber. The chamber may be configured to be held at a pressure below a supercritical pressure of the supercritical fluid (below a threshold pressure required to maintain the supercritical fluid in a supercritical state). The chamber may be configured to be held at atmospheric pressure. The apparatus may also comprise a hopper configured to feed items to be coated into the chamber.

The apparatus may further comprise an outlet through which items coated with precipitated particles are removed from the apparatus.

Spraying a mixture of supercritical fluid such as supercritical carbon dioxide and a solution comprising dissolved material for forming particles into a chamber at a pressure below supercritical pressure of the supercritical fluid (for example atmospheric pressure) may enable improved production of particles. The supercritical fluid in the mixture may act as either or both of a supercritical anti-solvent and an atomization enhancer. A rapid pressure drop as the mixture is sprayed into the chamber through the nozzle may cause droplets of the solution to be formed. Due to the below supercritical pressure in the chamber, the droplets may then rapidly dry (for example, prior to contacting the one or more items within the chamber) to form particles. Momentum of the depressurized supercritical fluid may also provide a drying effect for the droplets. The pressure (for example atmospheric pressure) of the chamber may therefore provide a dual effect in aiding the precipitation of particles. A chamber at below supercritical pressure may reduce or avoid the need for specialized high pressure equipment, thereby reducing equipment costs and complexity, and improving process safety.

The apparatus may enable the precipitated particles to be captured on one or more items located within the chamber soon after precipitation. That may reduce opportunity for the particles to agglomerate or coalesce. The particles may therefore be coated onto the one or more items substantially individually, resulting in a homogeneous particle coating. That may be particularly beneficial for nanoparticle coatings. Nanoparticles have a tendency to agglomerate which can have a deleterious effect on rheological properties of the nanoparticles such as compressibility and flowability. An apparatus which performs both particle production and particle coating may avoid the need for intermediate equipment to isolate the particles prior to coating (such as filters or electrostatic chambers). An apparatus configured to capture particles soon after precipitation may also improve a process yield (particularly in respect of nanoparticles).

A chamber configured to be held at a pressure below a supercritical pressure (for example atmospheric pressure) may also be beneficial for use in a continuous process. Items to be coated may be fed into the chamber from the hopper (and coated items removed from the chamber), without substantially affecting operating conditions within the chamber. Operating conditions for a highly pressurized chamber may be compromised on feeding items into the chamber and removing coated items from the chamber. That effect is particularly significant for a chamber configured to be held at atmospheric pressure.

The hopper may be disposed substantially on a top portion of the chamber. The hopper being disposed on a top portion of the chamber enables items to be gravity fed into the chamber, either continuously or intermittently. Gravity feeding may enable a simple, low-cost implementation for feeding items to the chamber to improve process performance. The one or more items may capture precipitated particles as the items travel through the chamber by falling under gravity.

The apparatus may further comprise a cyclone separator for collecting items coated with precipitated particles. The cyclone separator may be disposed within the chamber, or may be located externally of the chamber. The cyclone separator may be in fluid communication with the chamber. A cyclone separator may enable efficient separation and collection of items coated with precipitated particles, particularly in a continuous process.

The at least one nozzle may be located substantially on a side portion of the chamber. That may prevent the nozzle from interfering with the hopper if the hopper is disposed on a top portion of the chamber. That may simplify construction of the apparatus. The at least one nozzle may be configured to orient a spray of the mixture to promote a helical travel path of items and precipitated particles through the chamber. That may increase a circulation time of the items and precipitated particles within the chamber compared to a direct linear travel path through the chamber. Increasing a circulation time may improve one or more of drying of the items, drying of the precipitated particles and particle loading onto the items.

The apparatus may comprise a plurality of nozzles located substantially on a side portion of the chamber. The plurality of nozzles may be distributed over a length of height of the chamber. As the items travel through the chamber (for example, falling under gravity from a top portion of the chamber), the items may be coated with progressively more and more particles from sprays of successive nozzles as the items approach a bottom of the chamber. Locating nozzles on a top portion of the chamber would result in items fed into the chamber falling increasingly further away from precipitated nanoparticles, providing only a small spatial area within the chamber for items to be efficiently coated. A plurality of nozzles located on a side portion of the chamber and distributed over a length or height of the chamber may overcome that issue, as particles are precipitated at multiple locations along the items' travel path through the chamber.

Additionally or alternatively, the plurality of nozzles may be distributed over a circumference or perimeter of the chamber. The plurality of nozzles may be arranged to orient the mixture sprays to cooperate with one another to promote a helical travel path of items and precipitated particles through the chamber. The plurality of nozzles may be uniformly or non-uniformly distributed across a side portion of the chamber. The plurality of nozzles may be arranged in a substantially helical pattern across a side portion of the chamber.

A plurality of nozzles configured to spray a plurality of mixture sprays in a number of different directions may improve homogeneity of the particle coating. That may also prevent or inhibit precipitated particles from being captured on internal walls of the chamber. The precipitated particles and items may be substantially confined to a region of the chamber away from the walls by differently oriented sprays of mixture from the plurality of locations. That may increase a likelihood of the precipitated particles being captured on one or more items within the chamber, increasing process yield and efficiency.

The chamber may further comprise at least one inlet for providing a flow of drying gas. The supercritical anti-solvent and/or atomisation enhancement properties of supercritical carbon dioxide may assist or enhance a spray-drying process.

The formation of droplets due to the rapid pressure drop experienced by the mixture as it passes through the nozzle means that solvent evaporation may be rapid, resulting in rapid precipitation of particles. Integrating supercritical anti-solvent behaviour with a spray-drying process may further increase a rate of solvent evaporation. That may further enable particles to be rapidly produced.

Typically, spray-drying can be used to form micron sized particles (conventional spray-drying) or nanosized particles (nano spray-drying). As discussed above, nanoparticles often agglomerate if not isolated or captured on an item to be coated soon after being produced. That can result in a low processing yield for nano spray-drying, and subsequently a non-homogeneous coating on one or more coated items due to agglomerated nanoparticles. Integrating spray-drying and particle coating into a single process may improve process yield and provide a substantially homogeneous particle coating.

The at least one inlet may be located substantially on a top portion of the chamber. That may enable the flow of drying gas to be oriented in substantially the same direction as a direction of travel of items within the chamber. That may avoid the flow of drying gas opposing or even reversing a direction of travel of items within the chamber (which may disrupt a continuous coating process).

The at least one inlet may be located substantially on a side portion of the chamber. That may prevent the at least one inlet from interfering with the hopper if the hopper is disposed on a top portion of the chamber. That may simplify construction of the apparatus. The at least one inlet may be configured to orient a flow of drying gas to promote a helical travel path of items and precipitated particles through the chamber. That may increase a circulation time of the items and precipitated particles within the chamber compared to a direct linear travel path through the chamber. Increasing a circulation time may improve one or more of drying of the items, drying of the precipitated particles and particle loading onto the items.

The apparatus may comprise a plurality of inlets located substantially on a side portion of the chamber. The plurality of inlets may be distributed over a circumference or perimeter of the chamber. Additionally or alternatively, the plurality of inlets may be distributed over a length or height of the chamber. The plurality of inlets may be arranged to orient the flows of drying gas to cooperate with one another to promote a helical travel path of items and precipitated particles through the chamber. The plurality of inlets may be distributed uniformly or non-uniformly across a side portion of the chamber. The plurality of inlets may be arranged in a substantially helical pattern across a side portion of the chamber. In addition or alternatively to increasing a circulation time within the chamber, a plurality of inlets configured to provide multiple flows of drying gas oriented in a number of different directions may prevent or inhibit precipitated particles from being captured on internal walls of the chamber. The precipitated particles and items may be substantially confined to a region of the chamber away from the walls by differently oriented flows of drying gas. That may increase a likelihood of the precipitated particles being captured on one or more items within the chamber, increasing process yield and efficiency.

The apparatus may comprise at least one first nozzle configured to spray a first mixture into the chamber. The first mixture may comprise supercritical fluid and a solution comprising a first dissolved material for forming particles. The apparatus may comprise at least one second nozzle configured to spray a second mixture into the chamber. The second mixture may comprise supercritical fluid and a solution comprising a second dissolved material for forming particles.

A plurality of nozzles configured to spray different mixtures may enable the apparatus to produce particle coatings which have combinations of properties or tailored properties. For example, if the particles are or comprise multiple different API nanoparticles, multiple APIs may be coated onto excipient carrier particles. That may enable personalised drug combinations which may reduce the number of tablets an individual is required to take. Alternatively, for non-medical or non-medicinal applications, multiple different particle types may enable one or more of mechanical properties, chemical properties, electrical properties and optical properties (and optionally other properties) of a coating to be tailored.

The chamber may have or comprise a modular construction. The chamber may comprise one or more chamber segments. Each chamber segment may be configured to connect to one or more other chamber segments. The chamber segments may be configured to connect to one another end to end. Each chamber segment may have or comprise the same cross-sectional shape or profile (for example, circular, triangular, square, rectangular or higher polygon). Each chamber segment may have or comprise a substantially prismatic shape. Connecting a plurality of chamber segments to one another may provide a larger chamber in which one or more items may be coated.

Each chamber segment may have or comprise a substantially identical construction to the other chamber segments. Each chamber segment may comprise one or more nozzles. An arrangement or location of the one or more nozzles on each of the chamber segments may be substantially identical. The one or more nozzles may be located on a side portion of the chamber segments.

A modular chamber construction may enable a chamber size to be altered, for example increased or decreased. A chamber size may need to be altered depending on a required performance of the apparatus. For example, a plurality of chamber segments connected to one another may enable a chamber length to be increased. That may increase a length of a travel path of the items within the chamber, increasing a time spent by the items within the chamber. An increased travel path length may enable increased particle loading onto the items.

The apparatus may comprise a pump for maintaining an operating pressure (for example atmospheric pressure) in the chamber.

The apparatus of the second aspect may comprise one or more optional features of the method of the first aspect, and vice versa.

According to a third aspect, there is provided a method of producing a particle coating on one or more items. The method may comprise mixing supercritical fluid with a solution comprising dissolved material for forming particles. The method may also comprise spraying the mixture into a precipitation chamber to precipitate particles. The chamber may be at a pressure below a supercritical pressure of the supercritical fluid (below a threshold pressure required to maintain the supercritical fluid in a supercritical state). The chamber may be at substantially atmospheric pressure. The method may comprise capturing the precipitated particles on items located within the chamber.

The method of the third aspect may comprise one or more optional features of the method of the first aspect and the apparatus of the second aspect, and vice versa.

According to a fourth aspect, there is provided an apparatus for producing a particle coating on one or more items. The apparatus may comprise a chamber. The apparatus may comprise at least one nozzle to spray a mixture of supercritical fluid and a solution comprising dissolved material for forming particles into the chamber. The chamber may be configured to be held at a pressure below a supercritical pressure of the supercritical fluid (below a threshold pressure required to maintain the supercritical fluid in a supercritical state). The chamber may be at atmospheric pressure.

The apparatus of the fourth aspect may comprise one or more optional features of the method of the first aspect, the apparatus of the second aspect and the method of the third aspect, and vice versa.

Optional features of any of the above aspects may be combined with the features of any other aspect, in any combination. For example, features described in connection with the method of the first aspect may have corresponding features definable with respect to the apparatus of the second aspect or the coated carrier particle of the third aspect, and these embodiments are specifically envisaged. Features which are described in the context or separate aspects and embodiments of the invention may be used together and/or be interchangeable wherever possible. Similarly, where features are, for brevity, described in the context of a single embodiment, those features may also be provided separately or in any suitable sub-combination.

BRIEF DESCRIPTION OF THE DRAWINGS

The invention will now be described by way of example with reference to the accompanying drawings in which.

Like reference numbers and designations in the various drawings may indicate like elements.

DETAILED DESCRIPTION

Figure 1:
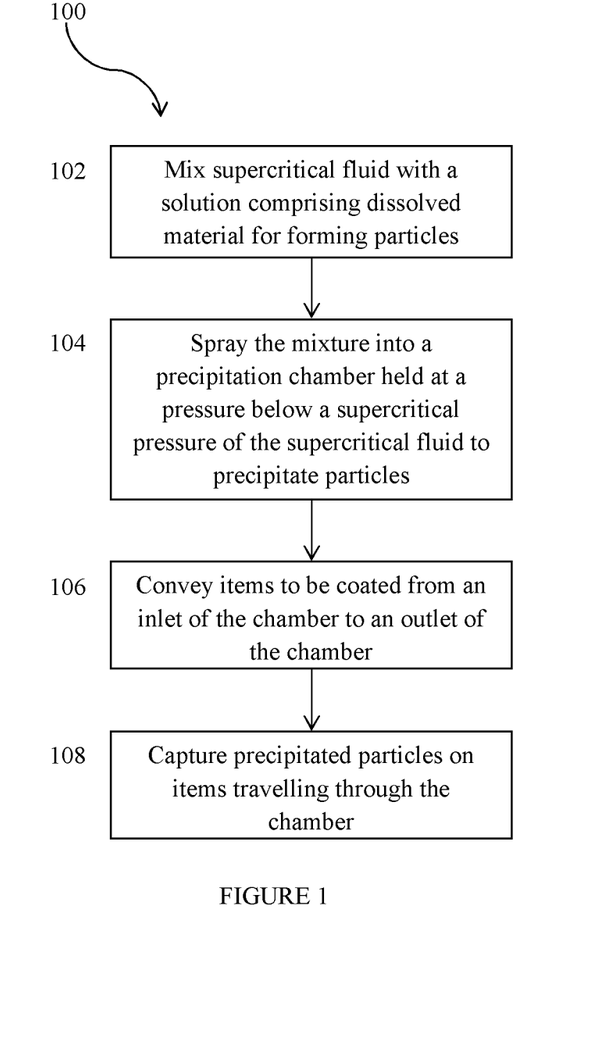
FIG. 1 shows an embodiment of a method for producing a nanoparticle coating on one or more items in accordance with the invention.

FIG. 1 shows an embodiment of a method 100 for producing a particle coating on one or more items.

The method 100 comprises mixing supercritical carbon dioxide with a solution comprising dissolved material for forming particles at step 102 (although other supercritical fluids may be used instead). The method 100 further comprises spraying the mixture into a precipitation chamber held at a pressure below a supercritical pressure of the supercritical fluid (for example atmospheric pressure) to precipitate particles at step 104. The method 100 also comprises conveying items from an inlet of the chamber to an outlet of the chamber at step 106. The method 100 comprises capturing precipitated particles on items travelling through the chamber at step 108.

Figure 2:
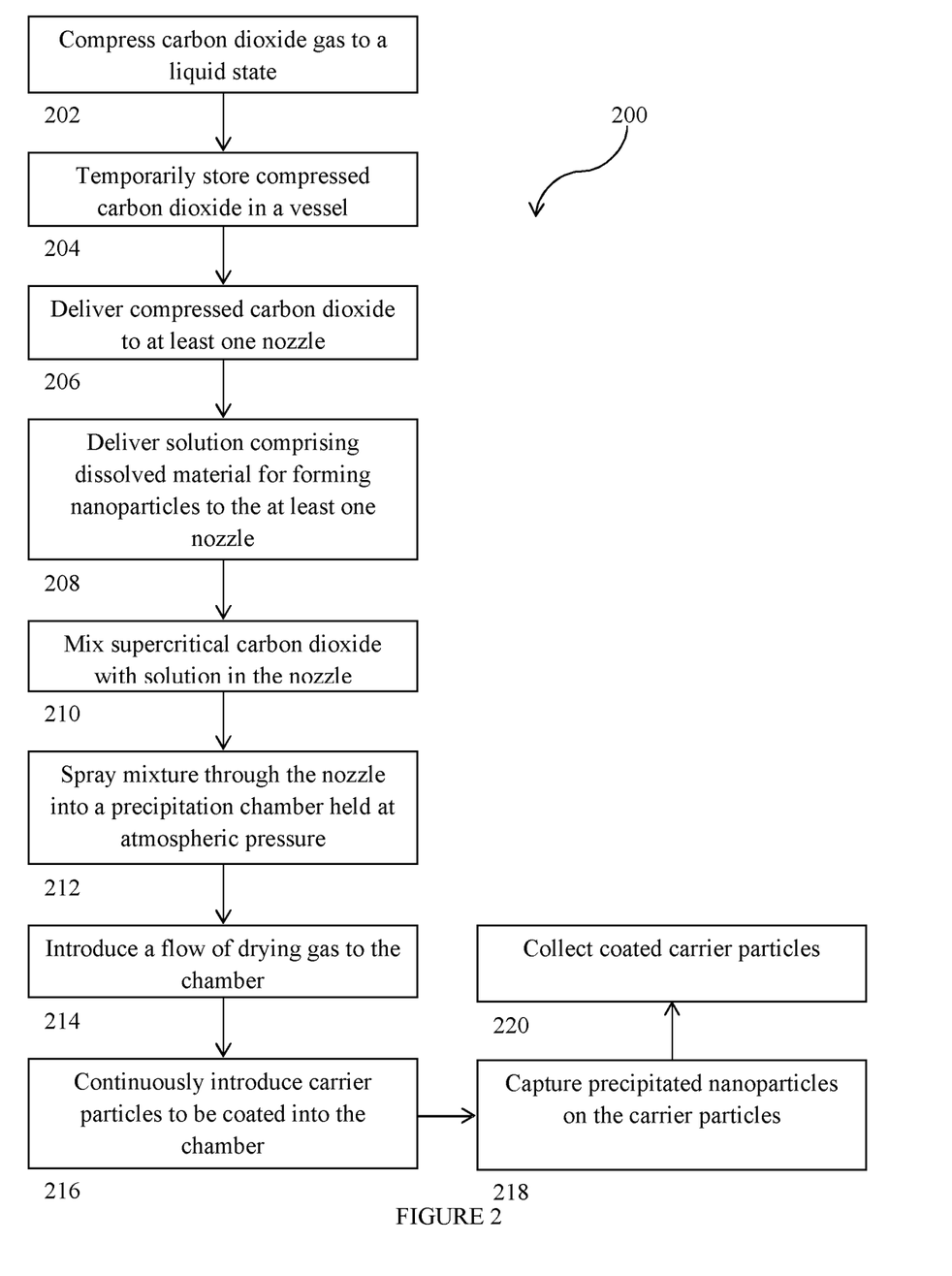
FIG. 2 shows an embodiment of a method for producing an API nanoparticle coating on carrier particles in accordance with the invention.

FIG. 2 shows an embodiment of a method 200 for producing a nanoparticle coating on one or more items, in line with the method 100 as set out above. The method 200 may carried out using, and is described with respect to, an apparatus 300 shown in FIG. 3.

Figure 3:
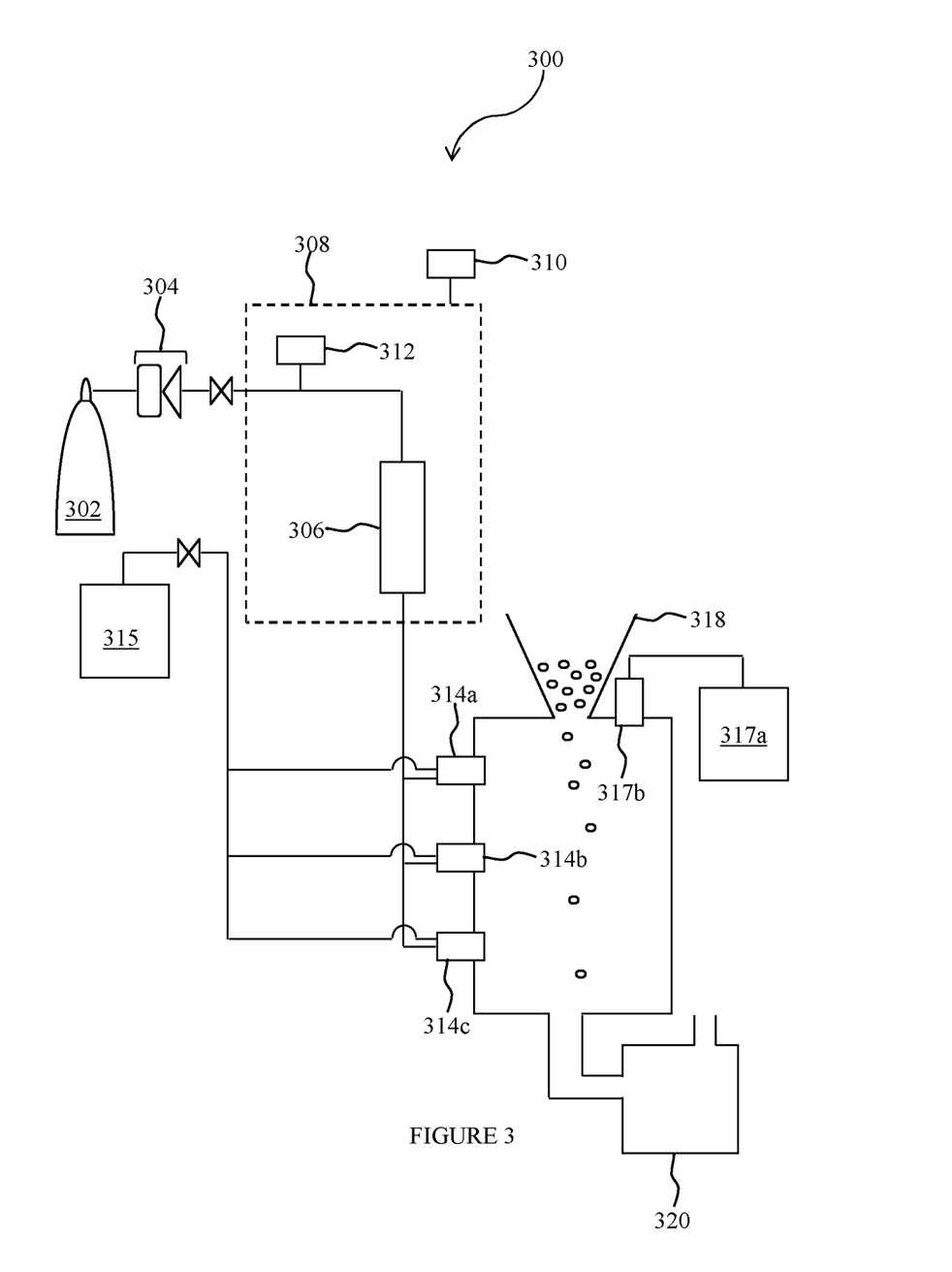
FIG. 3 shows an embodiment of an apparatus for use in the method of FIG. 1 or FIG. 2 in accordance with the invention.

Step 202 of the method 200 comprises compressing carbon dioxide gas to a liquid state. In the embodiment shown, carbon dioxide from a cylinder 302 is compressed using a pump 304. In the embodiment shown, the pump 302 is a SFE Process Dose HPP 400-C pump, but any suitable pump may be used.

Step 204 of the method 200 comprises temporarily storing the compressed carbon dioxide in a temperature controlled vessel 306. The temperature controlled vessel 306 is stored in a temperature controlled air chamber 308. The temperature of the vessel 306 is controlled by virtue of the vessel 306 being located in the temperature controlled air chamber 308. In the embodiment shown, the temperature controlled air chamber 308 is held at 60° C., but any suitable temperature may be used. A controller 310 is used to control the temperature in the air chamber 308. A pressure indicator 312 is used to monitor a pressure of the supercritical carbon dioxide. Any suitable pressure indicator may be used.

Step 206 of the method 200 comprises delivering the compressed carbon dioxide to a first nozzle 314a, second nozzle 314b and third nozzle 314c of the apparatus 300 respectively. Alternatively, the compressed carbon dioxide may be delivered directly to the nozzles 314a, 314b, 314c of the apparatus 300 without any intervening steps, such as temporary storage in a temperature controlled vessel 306. In the embodiment shown, three nozzles 314a, 314b, 314c are used, but any suitable number of nozzles may be used. Alternatively, the apparatus 300 may comprise only one nozzle 314 to which compressed carbon dioxide is delivered.

Step 208 of the method 200 comprises delivering a solution comprising dissolved material for forming nanoparticles from a storage vessel 315 to the nozzles 314a, 314b, 314c of the apparatus 300. In the embodiment shown, the solution comprises carbamazepine dissolved in methanol. The solution may alternatively comprise any active pharmaceutical ingredient (API), from any of classes I, II, III or IV (according to the biopharmaceutical classification system (BCS)), dissolved in an organic solvent. For example, the API may be or comprise one of carbamazepine, risperidone, ketoprofen and hydrochlorothiazide. The organic solvent may be or comprise an alcohol, for example methanol. Alternatively, the solution may comprise any suitable solvent in which any suitable material for forming nanoparticles is dissolved, depending on the desired properties of the nanoparticle coating to be formed. A plurality of different solutions may be delivered separately to separate nozzles 314, 314b, 314c. That may allow multiple different types of nanoparticle to be coated onto one or more items simultaneously in a single process. In the embodiment shown, the solution is delivered to the nozzles 314a, 314b, 314c using an Agilent Technologies 1260 Infinity II pump, but any suitable pump may be used. In the embodiment shown, the flow rate of solution delivered to the nozzles 314a, 314b, 314c is maintained between substantially 0.1 mL·min$^{-1}$ and substantially 2.0 mL·min$^{-1}$, but any suitable flow rate may be used depending, for example, on characteristics of the apparatus 300.

Step 210 of the method 200 comprises mixing supercritical carbon dioxide with the solution comprising dissolved material for forming nanoparticles in the nozzles 314a, 314b, 314c of the apparatus 300. In the embodiment shown, the nozzles 314a, 314b, 314c are coaxial nozzles having a mixing volume of approximately 0.1 cm$^3$. The solution and the compressed carbon dioxide are delivered to the nozzle 314 separately (for example, via separate fluid lines). In the embodiment shown, the nozzles 314a, 314b, 314c are maintained at a temperature of substantially 50° C. in order to heat the compressed carbon dioxide delivered to the nozzles 314a, 314b, 314c to a supercritical state, but any suitable temperature may be used. For example, the temperature may be dependent on the particular solvent used to dissolve the material for forming nanoparticles. In the embodiment shown, the solvent used is methanol which has a boiling point of 65° C. In the embodiment shown, supercritical carbon dioxide pressure is maintained between substantially 9 MPa and substantially 17 MPa, but any suitable pressure of supercritical carbon dioxide may be used. The nozzles 314a, 314b, 314c are heated using heating resistors (not shown) in close proximity to the nozzles 314a, 314b, 314c. The heating resistors may be controlled by a controller. However, any suitable heating means may alternatively be used. The supercritical carbon dioxide mixes with the solution in the mixing volume of the nozzles 314a, 314b, 314c.

The compressed carbon dioxide may alternatively be heated to supercritical conditions prior to being delivered to the nozzles 314a, 314b, 314c, for example using a heating coil enveloping a pipe containing compressed carbon dioxide. Additionally or alternatively, the solution may be mixed with supercritical carbon dioxide prior to being delivered to the nozzles 314a, 314b, 314c. The method 200 may therefore alternatively comprise delivering a pre-formed mixture of supercritical carbon dioxide and solution to the nozzles 314a, 314b, 314c, rather than separately delivering compressed or supercritical carbon dioxide and solution to the nozzles 314a, 314b, 314c. The nozzles 314a, 314b, 314c may therefore not be coaxial nozzles.

Steps 202 to 210 of the method 200 may be replaced by any suitable technique(s) for forming a mixture of supercritical carbon dioxide and solution comprising dissolved material for forming nanoparticles. Exactly how either or both i) the supercritical carbon dioxide, or ii) the mixture of supercritical carbon dioxide and solution are formed is not critical to the invention, as long as the mixture is formed before being introduced into a precipitation chamber 316.

Step 212 of the method 200 comprises spraying the mixture through the nozzles 314a, 314b, 314c into a precipitation chamber 316 to precipitate nanoparticles. It will be appreciated that means other than the nozzles 314a, 314b, 314c may be used to introduce the mixture into the chamber 316. The chamber 316 is held at atmospheric pressure. The mixture experiences a rapid pressure drop as the mixture passes through the nozzles 314a, 314b, 314c into the chamber 316. In the embodiment shown, the nozzles 314a, 314b, 314c comprise substantially circular nozzle orifices having a diameter of substantially 40 µm. Nozzles having nozzle orifices of any shape, for example square, rectangular, polygonal or other shapes may be used. Any nozzle orifice having a size so as to form nanoparticles on spraying the mixture into the chamber 316 may alternatively be used, for example a nozzle orifice size of substantially 150 µm or smaller. As the supercritical carbon dioxide depressurizes to form carbon dioxide gas due to the chamber 316 being at atmospheric pressure, nanodroplets (nanosized droplets) of the solution are formed. The supercritical carbon dioxide may therefore act to enhance atomisation of the solution as the mixture passes through the nozzles 314a, 314b, 314c into the chamber 316. The rapid pressure drop may work in conjunction with the anti-solvent effect of the supercritical carbon dioxide to form the nanodroplets. The chamber 316 being held at atmospheric pressure may also enable the nanodroplets to dry rapidly in order to precipitate nanoparticles. It will be appreciated that the same could be achieved by using a chamber 316 held at a pressure below a supercritical pressure of the supercritical fluid, enabling the supercritical fluid to depressurize on introduction to the chamber 316. The chamber 316 being held at atmospheric pressure may avoid the need for specialist equipment to pressurize or provide a vacuum in the chamber 316, further reducing cost and complexity.

Additionally or alternatively, process parameters other than nozzle orifice size may be selected or controlled to obtain particles of a desired size. For example, one or more of a flow rate of solution delivered to the nozzle 314, a flow rate of compressed carbon dioxide delivered to the nozzle 314, a density of supercritical carbon dioxide formed in the nozzle 314, a flow rate of drying gas introduced to the chamber 316 (discussed below), and a temperature inside the chamber 316 may influence a size of droplets formed by spraying the mixture through the nozzle 314. A size of the droplets in turn influences a size of particles produced by the method 200. Nanoparticles having a size of substantially 10 nm (or greater) may be produced by controlling one or more of the operating parameters accordingly.

Step 214 of the method 200 comprises introducing a flow of drying gas into the chamber 316. In the embodiment shown, the drying gas comprises nitrogen gas, although it will be appreciated any suitable gas or mixture of gases may be used as a drying gas (for example, carbon dioxide and/or nitrogen gas may be used). In the embodiment shown, the drying gas is introduced into the chamber 316 through an inlet 317b from a storage vessel 317a. In the embodiment shown, the flow rate of the nitrogen gas is substantially 0.4 mL·min$^{-1}$, but any suitable flow rate may be used. In the embodiment shown, the drying gas is introduced from a top portion of the chamber 316. Additionally or alternatively, the drying gas may be introduced from a side portion of the chamber 316 (discussed further below). Using a drying gas in conjunction with a rapid pressure drop may further increase a rate of solvent evaporation from the nanodroplets, leading to faster precipitation of nanoparticles. Alternatively, a flow of drying gas may not be introduced into the chamber 316, and nanoparticles may be precipitated using only the rapid pressure drop after spray of the mixture from the nozzles 314a, 314b, 314c, and ambient pressure of the chamber 316.

Step 216 of the method 200 comprises conveying carrier particles to be coated from an inlet of the chamber 316 to an outlet of the chamber 316. In the embodiment shown, the chamber 316 comprises a cylindrical shape, but the chamber 316 may comprise any suitable shape. The carrier particles are shown schematically in FIG. 3 and are not to scale. In the embodiment shown, the carrier particles comprise microcrystalline cellulose particles, but any suitable excipient or mixture of excipients may alternatively be used. The carrier particles are continuously introduced to the chamber 316 from a hopper 318. In the embodiment shown, the hopper 318 is disposed on a top portion of the chamber 316. That allows the carrier particles to be gravity fed into the chamber 316. Alternatively, the hopper 318 may be located elsewhere on the chamber 316, for example a side portion of the chamber 316. The carrier particles capture precipitated nanoparticles whilst passing through the spray from the nozzles 314a, 314b, 314c. The carrier particles may be fluidized within the chamber 316 due to momentum of depressurized carbon dioxide and a flow of drying gas within the chamber 316. Fluidized carrier particles may more effectively capture precipitated nanoparticles whilst travelling through the chamber 316. Capturing the precipitated nanoparticles on the carrier particles within the chamber 316 may mean that the precipitated nanoparticles are captured on the carrier particles substantially immediately or shortly after precipitation, before having a chance to agglomerate or coalesce. Nanoparticles can be difficult to process or manipulate after agglomeration. Capturing the nanoparticles shortly after precipitation may avoid the need to manipulate the nanoparticles to overcome interactions between nanoparticles.

Conveying the carrier particles from an inlet of the chamber 316 to an outlet of the chamber 316 may enable carrier particles to be continuously introduced to the chamber. That means that the apparatus 300 may run continuously, without the apparatus 300 needing to be placed in a non-operational state (for example, in between introducing different carrier particles to be coated to the chamber 316, or to remove coated items from the apparatus 300).

A size of an opening of the hopper 318 through which carrier particles are introduced into the chamber 316 may be controlled to control a feed rate of carrier particles into the chamber 316.

For example, the opening of the hopper 318 may be occluded (for example, partially) or expanded to decrease or increase a feed rate of the carrier particles respectively. The size of the opening of the hopper 318 may be controlled manually or automatically (for example using a controller).

In the embodiment shown, the nozzles 314a, 314b, 314c are disposed on a side portion of the chamber 316 and distributed uniformly over a length or height of the chamber 316. That may mean that the carrier particles are coated with progressively more and more nanoparticles whilst travelling through the chamber 316 (for example falling under gravity from a top portion of the chamber 316), enhancing the continuous nature of the process. It may also improve homogeneity of the nanoparticle coating by increasing opportunity for the carrier particles to capture precipitated nanoparticles. The nozzles 314a, 314b, 314c may alternatively be distributed non-uniformly over the height of the chamber 316, but may provide substantially the same benefit. In the embodiment shown, the nozzles 314, 314b, 314c are shown disposed on the same side of the chamber 316. Alternatively, the nozzles 314b, 314b, 314c may be disposed on different sides of the chamber 316. For example, the nozzles 314a, 314b, 314c may be distributed around a perimeter of the chamber 316 (in addition to being distributed over a height of the chamber 316). One or more nozzles may alternatively be disposed or located on a top portion of the chamber 316.

Alternatively, the method 200 may comprise capturing precipitated nanoparticles on one or more items as the items pass through the chamber 316. The one or more items may be or comprise a medical implant, for example a joint replacement implant or a stent. Alternatively, the one or more items may be or comprise other non-medical or non-medicinal items for which a nanoparticle coating is required. Larger items (for example, joint replacement implants) may not travel through the chamber 316 by falling under gravity, but may instead be supported and conveyed through the chamber 316 (for example, may be supported on a structure such as a belt which passes through the chamber 316). A speed of the support structure through the chamber 316 may be altered analogously to altering a feed rate of carrier particles through the hopper 318.

Step 220 of the method 200 comprises collecting the coated carrier particles. In the embodiment shown, the coated carrier particles are collected using a cyclone separator 320. In the embodiment shown, the coated carrier particles are conveyed from an outlet of the chamber 316 to the cyclone separator 320 for collection. The cyclone separator 320 separates the coated carrier particles from residual carbon dioxide, residual solvent and drying gas. The coated carrier particles settle at the bottom of the cyclone separator ready for collection, whilst the residual gases are removed using a pump (not shown), for example a vacuum pump, and expelled through an outlet in the cyclone separator. The pump may therefore maintain atmospheric pressure in the chamber 316. In the embodiment shown, the cyclone separator 320 is spatially separated from the chamber 316.

Alternatively, the cyclone separator 320 may be disposed within the chamber 316. The coated carrier particles may alternatively be collected in a different manner. For example, the coated carrier particles may simply collect on a floor of the chamber 316 ready to be removed from the apparatus 300. Residual gases (and optionally residual solvent) may be removed using a pump, for example a vacuum pump, to maintain atmospheric pressure in the chamber 316.

In the embodiment shown, a concentration of the carbamazepine solution may be varied between substantially 20 mg·L$^{-1}$ and substantially 60 mg·L$^{-1}$. Those concentrations are near to but not above a saturation limit of the solution (at the operating parameters set out as described above), and are referred to herein as saturated solutions. It has been found that undersaturated solution results in the production of amorphous nanoparticles using the method 200. In contrast, supersaturated solution (having a concentration above a saturation limit) results in precipitation of crystalline nanoparticles in the nozzles 314a, 314b, 314c, which may lead to blockage of the nozzles 314a, 314b, 314c. Saturated solution results in liquid-like cluster formation (nucleation) of the nanoparticles in the nozzles 314a, 314b, 314c. The clusters convert to crystals upon passing through the nozzles 314a, 314b, 314c due to formation of nanodroplets which dry rapidly under atmospheric pressure in the chamber 316. In addition, as the mixture of supercritical carbon dioxide and solution is formed in the nozzles 314a, 314b, 314c in the embodiment shown, there is not sufficient time for nanoparticles to crystallise in the nozzles 314a, 314b, 314c, as residence time of the mixture in the nozzles 314a, 314b, 314c is of the order of milliseconds. Alternatively, any suitable concentration of solution may be used. For example, if crystalline nanoparticles are not required and amorphous nanoparticles will be satisfactory, an undersaturated solution may be used. A saturated solution may comprise different concentrations for different nanoparticle materials and/or different solvents. A saturated solution may also comprise different concentrations depending on operating parameters such as temperature and pressure (which may determine a saturation limit of the solution).

Varying a concentration of the solution may enable nanoparticle loading onto the carrier particles to be altered or controlled. In the embodiment shown, nanoparticle loading onto the carrier particles is substantially 5% for a solution concentration of substantially 20 mg·L$^{-1}$, whereas nanoparticle loading onto the carrier particles is substantially 25% for a solution concentration of substantially 60 mg·L$^{-1}$. A lower concentration of the solution may alternatively be used, which may further reduce nanoparticle loading but may result in an undersaturated solution being used, producing amorphous nanoparticles. As above, a range of concentrations forming a saturated solution may be different for different nanoparticles and/or different solvents. Alternatively, nanoparticle loading onto the carrier particles can be altered or controlled by varying a mass of material for forming nanoparticles introduced into the chamber 316 without changing a concentration of the solution. For example, the solution may be sprayed into the chamber 316 for a greater length of time, which will result in a greater mass of material for forming nanoparticles being introduced to the chamber 316. A greater mass of material for forming nanoparticles introduced into the chamber 316 may result in an increased nanoparticle loading onto the carrier particles, and vice versa. Introducing a greater mass of material for forming nanoparticles into the chamber 316 may increase the possible amount of nanoparticle material that may be captured by the carrier particles (or other items). Controlling loading of nanoparticles onto the carrier particles, particularly in the case of API or anti-bacterial drug nanoparticles, may enable the dose of API or anti-bacterial drug to be accurately controlled.

The method 200 described above relates to production of a nanoparticle coating on one or more items. However, the methods 100, 200 described above are not limited to producing nanoparticles or nanoparticle coatings. Different particle sizes may be produced using the methods 100, 200, for example by altering a nozzle orifice size of the nozzles 314a, 314b, 314c through which the mixture is sprayed into the chamber 316. A larger nozzle orifice size may produce larger droplets of solution as the mixture enters the precipitation chamber 316. Conversely, smaller nozzle orifices may produce smaller droplets of solution as the mixture enters the precipitation chamber 316. The rapid pressure drop as the mixture is sprayed into the chamber 316 through the nozzles 314a, 314b, 314c may result in rapid evaporation of the solvent in the droplets, irrespective of the droplet size. The rate of solvent evaporation may be further increased by a flow of drying gas. The particle size produced may therefore be substantially dictated by a size of solution droplets formed by spraying the mixture through the nozzles 314a, 314b, 314c.

Figure 4:
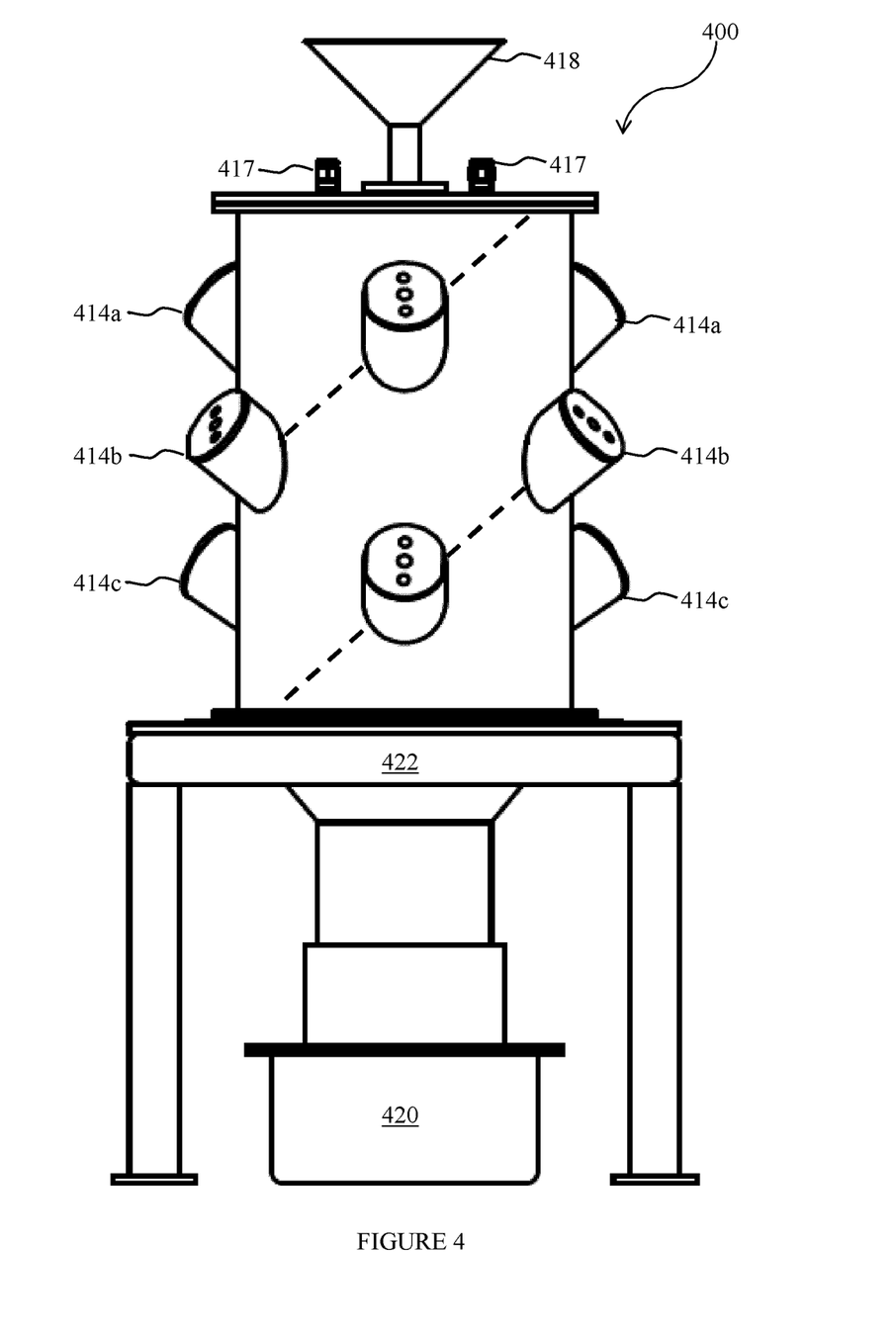
FIG. 4 shows an embodiment of an apparatus for use in the method of FIG. 1 or FIG. 2 in accordance with the invention.

FIG. 4 shows an embodiment of an apparatus 400 for producing a nanoparticle coating on one or more items, for example using the methods 100, 200 described above. The apparatus 400 comprises a chamber 416, a hopper 418 and a plurality of nozzles 414. In the embodiment shown, the chamber 416 comprises a cylindrical shape, but the chamber 416 may comprise any suitable shape. The nozzles 414 are substantially uniformly distributed both over a height or length of the chamber 416, and around a perimeter of the chamber 316. The nozzles 414 are arranged in a substantially helical pattern across a side portion of the chamber 416, as indicated by the dashed lines between the nozzles 414. That arrangement may provide a volume or region within the chamber 416 in which the precipitated particles are concentrated. The region may prevent contact of the items and precipitated particles with internal walls of the chamber 416. The region may be symmetrical as a result of the substantially uniform distribution of the nozzles 414 around the chamber 416. Carrier particles or other items may be introduced to the chamber 416 via the hopper 418. The hopper 418 is disposed on a top portion of the chamber 416, enabling the items to be gravity fed into the chamber 416. The items travel through the concentrated region of precipitated particles and become coated.

In the embodiment shown, the nozzles 414 are arranged in three nozzle layers 414a, 414b, 414c. In the embodiment shown, the nozzles in the top or first nozzle layer 414a are oriented at an angle of substantially 130° (where 0° is a vertical direction, for example parallel to a side wall or side portion of the chamber 416). The nozzles in the second nozzle layer 414b are oriented at an angle of substantially 125°. The nozzles in the third layer 414c are oriented at an angle of substantially 120°. The angles for each nozzle layer have been optimised using computational fluid modelling to optimise a helical travel path of precipitated particles and items through the chamber 416 having the specific cylindrical shape shown in FIG. 4. A chamber 416 having or comprising a different shape may require nozzles oriented at different angles to those shown in order to promote a helical path through the chamber 416. Alternatively, the nozzles in each nozzle layer 414a, 414b, 414c may be oriented at substantially the same angle. One or more of the nozzles may be oriented at a different angle to the other nozzles. The nozzles may be oriented at an angle of substantially 90° (substantially perpendicular to a vertical direction of 0°) or greater. That may prevent a mixture spray from the nozzles 414 from opposing a direction of travel of the items through the chamber 416.

The apparatus 400 also comprises inlets 417 for providing a flow of drying gas into the chamber 416. In the embodiment shown, the inlets 417 are disposed on a top portion of the chamber 416. Alternatively, the drying gas inlets 417 may be located on a side portion of the chamber 416. The drying gas inlets 417 may be arranged similarly to the nozzles 414 (for example, arranged promote a helical travel path of items and precipitated particles through the chamber 416, such as in a substantially helical pattern). For example, a drying gas inlet 417 may be located adjacent to each nozzle 414 on a side portion of the chamber 416.

In the embodiment shown, the chamber 416 is supported on a platform 422. A cyclone separator 420 is located below the platform. The cyclone separator 420 is in fluid communication with the chamber 416. Once the items (for example, carrier particles) have travelled through the chamber 416 and been coated with precipitated particles, the items enter the cyclone separator 420 and collect at a bottom of the cyclone separator 420. Supporting the chamber 416 on a platform 422 above the cyclone separator 420 allows for the apparatus 400 to have an inline arrangement. The height of the platform 422 may depend on a height of the cyclone separator 420. Of course, it is not essential that the chamber 416 be supported on a platform 422. The chamber 416 may be supported by the cyclone separator 420 itself (for example, in an inline arrangement), or both the chamber 416 and the cyclone separator may be located on the same surface (for example, the floor).

Figure 5:
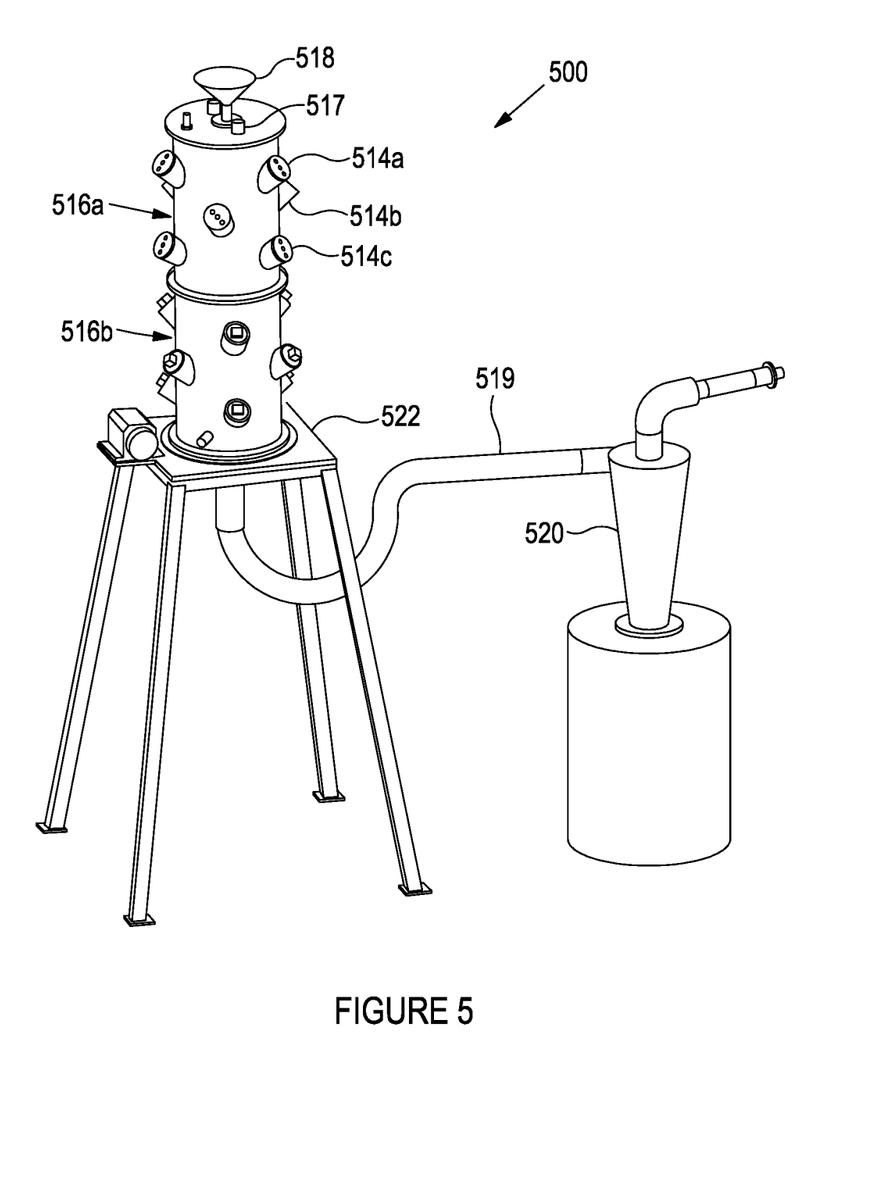
FIG. 5 shows an embodiment of an apparatus for use in the method of FIG. 1 or FIG. 2 in accordance with the invention.

FIG. 4 shows an embodiment of an apparatus 500 for producing a nanoparticle coating on one or more items, for example using the methods 100, 200 described above. The apparatus 500 is substantially similar to the apparatus 400 described above, and like reference numerals have been used to indicate like features.

The apparatus 500 comprises a chamber 516. The chamber 516 comprises a first chamber segment 516a and a second chamber segment 516b. A plurality of nozzles 514 are located on a side portion of the first chamber segment 516a. As described above with respect to FIG. 4, the nozzles are arranged in three nozzle layers 514a, 514b, 514c. A plurality of nozzles 514 are also located on a side portion of the second chamber segment 516b. The second chamber segment 516b is substantially identical in construction to the first chamber segment 516a. In the embodiment shown, each of the chamber segments 516a, 516b has a substantially cylindrical shape. Alternatively, each chamber segment 516a, 516b may have or comprise a substantially prismatic construction (for example, having a circular, triangular, square, rectangular or higher polygon cross-sectional shape or profile).

In the embodiment shown, the chamber 516 therefore has a modular construction. One or more additional chamber segments may be added to the chamber 516 in order to increase a size of the chamber 516. For example, a third chamber segment may be attached in between the first chamber segment 516a and the second chamber segment 516b. In the embodiment shown, adjacent chamber segments 516a, 516b are attached to one another end to end. The third chamber segment may have or comprise a substantially identical construction to the first and second chamber segments 516a, 516b. That may increase a length or height of the chamber 516. Increasing a length of the chamber 516 may increase a travel path length (and therefore travel time) of items travelling through the chamber 516. In the embodiment shown, each chamber segment 516a, 516b comprises nozzles 514 located on a side portion of the chamber segment 516a, 516b. Increasing a length of the chamber 516 may therefore increase particle loading onto the items passing through the chamber 516, as the items may interact with the mixture sprays from a greater number of nozzles 514 (from a plurality of chamber segments 516*a*, 516*b*) whilst travelling through the chamber 516. One or more chamber segments 516*a*, 516*b* may be removed from the chamber 516 to reduce a size of the chamber 516, if required.

In the embodiment shown, the chamber 516 is supported on a platform 522. The apparatus 500 also comprises a cyclone separator 520. The chamber 516 is held at a greater height than the cyclone separator 520. However, unlike the apparatus 400 described above, the chamber 516 and cyclone separator 520 are not arranged in line with one another in the embodiment shown. Rather, the cyclone separator 520 is laterally displaced from the chamber 516. The chamber 516 is in fluid communication with the cyclone separator 520 via a conduit 519. The conduit 519 is configured to convey coated items from the chamber 516 to the cyclone separator 520. The conduit 519 is connected at a first end to a bottom of the chamber 516, and at a second end to a side of the cyclone separator 520. An outlet for residual gases and solvent is provided in a top of the cyclone separator 520.

From reading the present disclosure, other variations and modifications will be apparent to the skilled person. Such variations and modifications may involve equivalent and other features which are already known in the art of particle coating, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The applicant hereby gives notice that new claims may be formulated to such features and/or combinations of such features during the prosecution of the present application or of any further application derived therefrom. Features of the devices and systems described may be incorporated into/used in corresponding methods. Where features are disclosed in connection with one embodiment of a particle coating method, it should be appreciated that any one or more or all of the same features may be incorporated in other embodiments of particle coating methods, instead of or in addition to the features described for the particular embodiment. That is, any and all combinations of features are envisaged, and are envisaged to be interchangeable, replaceable, added or removed.

For the sake of completeness, it is also stated that the term "comprising" does not exclude other elements or steps, the term "a" or "an" does not exclude a plurality, a single processor or other unit may fulfil the functions of several means recited in the claims and any reference signs in the claims shall not be construed as limiting the scope of the claims.

The invention claimed is:

1. A method of producing a particle coating on one or more items, the method comprising:
   mixing a supercritical fluid with a solution comprising dissolved material for forming particles;
   spraying the mixture into a precipitation chamber to precipitate particles, wherein the chamber is at a pressure below a supercritical pressure of the supercritical fluid;
   conveying items to be coated from an inlet of the chamber to an outlet of the chamber by gravity feeding items to be coated into the chamber using a hopper; and
   capturing the precipitated particles on items within the chamber.

2. The method of claim 1, comprising introducing the items substantially from a top portion of the chamber.

3. The method of claim 2, comprising controlling a feed rate of items introduced to the chamber.

4. The method of claim 1, comprising capturing the precipitated particles on carrier particles, and optionally wherein the carrier particles comprise microcrystalline cellulose.

5. The method of claim 1, comprising:
   mixing the supercritical fluid with a first solution comprising a first dissolved material for forming particles to form a first mixture, and spraying the first mixture into the chamber to precipitate particles of a first material; and
   mixing the supercritical fluid with a second solution comprising a second dissolved material for forming particles to form a second mixture and spraying the second mixture into the chamber to precipitate particles of a second material.

6. The method of claim 1, comprising introducing a flow of drying gas into the chamber, and optionally comprising:
   i) introducing a flow of drying gas substantially from a top portion of the chamber; and/or
   ii) introducing a flow of drying gas substantially from a side portion of the chamber.

7. The method of claim 1, comprising collecting items coated with precipitated particles, and optionally using a cyclone separator.

8. The method of claim 1, comprising spraying the mixture substantially from a side portion of the chamber.

9. The method of claim 1, comprising:
   i) spraying the mixture through at least one nozzle into the chamber to precipitate particles, and optionally wherein a nozzle orifice size of the nozzle is substantially 50 μm or smaller; and/or
   ii) mixing the supercritical fluid with the solution in at least one nozzle, and/or wherein the at least one nozzle comprises a coaxial nozzle.

10. The method of claim 1, wherein the solution comprises an active pharmaceutical ingredient dissolved in an organic solvent, and optionally wherein:
    i) the active pharmaceutical ingredient comprises one of carbamazepine, risperidone, ketoprofen and hydrochlorothiazide; and/or
    ii) the organic solvent comprises an alcohol, and optionally wherein the alcohol is methanol.

11. The method of claim 1, wherein the solution comprises a saturated solution.

12. An apparatus for producing a particle coating on one or more items, the apparatus comprising:
    a chamber;
    at least one nozzle configured to spray a mixture of supercritical fluid and a solution comprising dissolved material for forming particles into the chamber;
      wherein the chamber is configured to be held at a pressure below a supercritical pressure of the supercritical fluid; and
    a hopper configured to feed items to be coated into the chamber.

13. The apparatus of claim 12, further comprising an outlet through which items coated with precipitated particles are removable from the apparatus.

14. The apparatus of claim 12, wherein the hopper is disposed substantially on a top portion of the chamber.

15. The apparatus of claim 12, further comprising a cyclone separator for collecting items coated with precipitated particles.

16. The apparatus of claim 12, wherein the at least one nozzle is located substantially on a side portion of the chamber.

17. The apparatus of claim 12, wherein the chamber further comprises at least one inlet for receiving a flow of drying gas, and optionally wherein the at least one inlet is located on at least one of substantially a top portion of the chamber and substantially a side portion of the chamber.

18. The apparatus of claim 12, comprising:
    at least one first nozzle configured to spray a first mixture into the chamber, the first mixture comprising the supercritical fluid and a solution comprising a first dissolved material for forming particles; and
    at least one second nozzle configured to spray a second mixture into the chamber, the second mixture comprising supercritical fluid and a solution comprising a second dissolved material for forming particles.

19. The apparatus of claim 12, further comprising a pump for maintaining an operating pressure in the chamber.

* * * * *